(12) United States Patent
Wambebe et al.

(10) Patent No.: US 6,365,201 B1
(45) Date of Patent: Apr. 2, 2002

(54) PHYTODRUG FOR MANAGEMENT OF PEPTIC ULCER AND METHODS OF PREPARING AND USING SAME

(75) Inventors: Charles O. N. Wambebe; Shingu K. Gamaniel, both of Abuja; Peter Akah, Nsukka; Dogara S. Fumen, Kaduna State; Hafsatu Shittu, Abuja, all of (NG)

(73) Assignee: National Institute for Pharmaceutical Research and Development, Abuja (NG)

( * ) Notice: Subject to any disclaimer, the term of this patent is extended or adjusted under 35 U.S.C. 154(b) by 0 days.

(21) Appl. No.: 09/606,305

(22) Filed: Jun. 29, 2000

Related U.S. Application Data

(60) Continuation of application No. 09/228,107, filed on Jan. 11, 1999, now Pat. No. 6,083,509, which is a division of application No. 08/906,937, filed on Aug. 6, 1997, now Pat. No. 6,086,882.

(51) Int. Cl.$^7$ ............................ A61K 35/78; A61K 9/48; A61K 9/20
(52) U.S. Cl. ..................... 424/774; 514/925; 514/926; 514/927; 424/465; 424/451
(58) Field of Search ............................... 424/195.1, 451, 424/464, 465, 774; 514/925, 926, 927

(56) References Cited

U.S. PATENT DOCUMENTS

| | | | |
|---|---|---|---|
| 5,124,360 A | 6/1992 | Larner et al. | 514/738 |
| 5,130,133 A | 7/1992 | Rajagopalan et al. | |
| 5,219,574 A | 6/1993 | Wehling et al. | 424/464 |
| 5,277,910 A | 1/1994 | Hidvegi | |
| 5,464,620 A | 11/1995 | Zhao | |

OTHER PUBLICATIONS

Nyarko et al., Phytotherapy. Research, vol. 7, pp. 1–4, 1993.
Addy, et al. Phytotherapy Research., vol. 6, pp. 25–28, 1992.
Addy, et al. Phytotherapy Research, vol. 2, pp. 192–195, 1988.

*Primary Examiner*—Christopher R. Tate
(74) *Attorney, Agent, or Firm*—Shook, Hardy & Bacon L.L.P.

(57) ABSTRACT

A phytochemical composition for management of peptic ulcer conditions in humans is provided. The composition is a hot water extract of powdered *Indigofera arrecta* plant leaves. The extract may be prepared by contacting the powdered leaves with hot water for a period of time, filtering the extraction mixture, concentrating the filtrate in vacuo and freeze drying the concentrated filtrate. The extract is admixed with magnesium carbonate, dried maize starch, talc and magnesium stearate to form a homogenous mass which is filled into capsules. The capsules are ingested orally to provide an analgesic effect. Also described are methods for making the extract and the methodology for using the extract.

6 Claims, No Drawings

PHYTODRUG FOR MANAGEMENT OF PEPTIC ULCER AND METHODS OF PREPARING AND USING SAME

CROSS REFERENCES TO RELATED APPLICATIONS

This application is a continuation of application Ser. No. 09/228,107 filed on Jan. 11, 1999, now U.S. Pat. No. 6,083,509, which in turn is a divisional of application Ser. No. 08/906,937 filed on Aug. 6, 1997, now U.S. Pat. No. 6,086,882.

Priority is claimed herein under 35 U.S.C. §119 from application no. RP.12581 filed in Nigeria on Aug. 12, 1996.

BACKGROUND OF THE INVENTION

1. Field of the Invention

The present invention relates to the field of phytodrugs, and in particular the invention relates to phytodrugs for management of peptic ulcer conditions in humans and methods of preparing and using same.

2. Prior Activities and Problems in the Field

Peptic ulcer has been defined as a benign lesion of gastric or duodenal mucosa occurring at a site where the mucosal epithelium is exposed to acid and pepsin. It is a gastrointestinal problem that has been prevalent in society. The occurrence of the disease has been associated with over-indulgence, inappropriate habit, anxiety and stress. Considerable energy and resources have been expended towards relieving symptoms of peptic ulcer which usually manifests as an excruciating pain, especially in the upper abdomen. For centuries neutralization of gastric acid secretion with antacids and H2-receptor antagonists, provide the only relief from the pains of peptic ulcer. The drugs are generally expensive. Consequently, the socio-economic impact of peptic ulcer disease on the society can only be imagined.

In the foregoing assertion, efforts have been made to find a suitable palliative and/or curative agent for the treatment of peptic ulcer conditions from medicinal plants.

It is estimated that approximately 10% of most populations globally will develop severe peptic ulcer conditions at some time during their lifetime. The lesions occur at all ages and affect both sexes.

Authorities estimate that at least five million people suffer from active peptic ulcers each year, and approximately 350,000 to 500,000 new cases are diagnosed annually in the United States alone. More than 600,000 patients are hospitalized in the U.S. each year for severe episodes. In approximately one-third of these cases serious complications occur, including intestinal obstruction, upper gastrointestinal hemorrhage and perforation. Furthermore, each year, over 6,000 deaths in the U.S. are directly caused by ulcer disorder. In addition, peptic ulcer conditions have been implicated as an indirect contributing factor in an additional 11,000 deaths each year.

In Nigeria, peptic ulcer conditions general afflict persons between the ages of 21 and 51. Duodenal ulcers have their greatest impact in middle age while gastric ulcers become increasingly more frequent with advancing age.

Peptic ulceration reflects an imbalance between the aggressive action of acid peptic secretions and the defensive forces that protect the mucosa. Gastric ulcers result from lowered defensive mechanisms and duodenal ulcers are the consequence of the destructive action of increased acid-peptic secretions.

Duodenal ulcers occur when gastric mucosa secretes substantial amounts of acid. Although some patients with duodenal ulcers have normal levels of acid secretion, on the average they are hyperchlorhydric. Gastric acid has two phases viz;

(1) a cephalic phase (vagally mediated) in which direct cholinergic stimulation of parietal cells induces gastrin release from the antrum, and (2) a less powerful antral phase when food enters the stomach, causing liberation of more gastrin from the antral mucosa.

Evidence that patients with duodenal ulcers have increased parietal cell mass also suggests a genetic predisposition even though experimental data indicate that parental cell hyperplasia can be acquired.

Gastric ulceration results from lowering of the gastric mucosal resistance. Principal among the defensive influences is mucous secretion. The increased frequency of gastric ulcers with advancing age might be compatible with progressive inability to secrete a protective layer of mucous. Chronic gastritis is a frequent concomitant of gastric ulcer, is associated with impaired mucous secretion and is also age-related. In experimental animals, it has been demonstrated that protein depletion, avitaminoses and general malnutrition increase the susceptibility to gastric ulceration.

There is now growing evidence that *Helicobactor pylori*, a bacterium may be the cause of duodenal ulcer. The evidence linking *Helicobactor pylori* with benign gastric ulcer is less convincing than duodenal ulcer. However, the consensus now is that the organism is probably important in the pathogenesis of 70% of gastric ulcers not attributable to the use of non-steroidal anti-inflammatory drugs (NSAIDS).

The symptoms evoked by peptic ulcers are exceedingly variable; some ulcers being virtually asymptomatic. Nausea and vomiting may be produced by either duodenal or gastric ulcers, but particularly by the latter. The most consistent manifestation is epigastric pain described variably as burning, gnawing or boring. Classically, the duodenal ulcer pain becomes most severe two or three hours after the last meal and persists until it is relieved by food or antacids. For this reason, the pain recurs in the middle of the night and requires a glass of milk or antacid for its relief. Such episodic pain may last for weeks or months only to abate, usually with regulated dietary regimen and therapy. Recurrence is often triggered by dietary indiscretions or stress and is usually very rapid and sometimes dramatic, presenting with hemorrhage or perforation. Death from peptic ulcer is usually due to bleeding or perforation. In addition, a high proportion of patients who die or whose ulcers bleed or perforate have no warning signals.

SUMMARY OF THE INVENTION

In accordance with the present invention, a new drug material extracted from *Indicofera arrecta* (family: papiolionaceae) plant leaves has been found to be effective in treating peptic ulcer conditions in humans. In particular the invention provides a composition for managing peptic ulcer conditions in humans comprising an extract of *Indigofera arrecta* plant leaves. Generally the composition will comprise a water extract of *Indigofera arrecta* plant leaves and in particular the composition may comprise a hot water extract of powdered *Indigofera arrecta* plant leaves.

The invention also provides a method for preparing a composition for managing peptic ulcer conditions in humans. In accordance with the invention, the method comprises providing a batch of *Indigofera arrecta* plant leaves; forming a powder from said leaves; and subjecting the powder to an extraction process to thereby form an extract containing a drug material effective for treating peptic ulcer conditions in humans. Generally speaking, water may be employed as an extraction solvent in the extraction process, and preferably the extraction process comprises contacting powdered *Indigofera arrecta* plant leaves with hot water.

In another aspect of the invention, an admixture is provided for treating peptic ulcer conditions in humans. The admixture may comprise a powdered extract of *Indigofera arrecta* plant leaves and an excipient carrier for said extract. Generally the extract may comprise a hot water extract of the plant leaves. Preferably, the excipient carrier may comprise a mixture of heavy magnesium carbonate, dried maize starch, talc and magnesium stearate, and in a particularly preferred form of the invention, the admixture comprises about 8 to 12 parts by weight of said leaf extract, about 170 to 180 parts by weight of said heavy magnesium carbonate, about 100 to 120 parts by weight of said dried maize starch and about 4 to 6 parts by weight of a talc/magnesium stearate mixture. Ideally the admixture comprises about 2.6 to about 4.3% by weight of said extract.

In yet another form the invention provides a method for treating a human afflicted with a peptic ulcer condition. In this form of the invention, the method comprises providing a batch *Indigofera arrecta* plant leaves, subjecting said batch of leaves to a hot water extraction process to thereby form an extract of said *Indigofera arrecta* plant leaves effective for treating a peptic ulcer condition, and treating a human afflicted with a peptic ulcer condition by administering said extract orally to said human. Generally the extraction process may comprise forming a powder from said batch of leaves and contacting said powder with hot water. Preferably, the extract is mixed with an expicient carrier material to form an admixture and the treating step comprises administering said admixture orally to said human. Ideally, the admixture of the invention comprises about 2.6 to about 4.3% by weight of said extract.

DETAILED DESCRIPTION OF PREFERRED EMBODIMENTS OF THE INVENTION

In accordance with the invention, a composition for treating and managing peptic ulcer conditions in humans is provided. The composition is prepared by extracting effective peptic ulcer inhibiting chemicals from the powdered leaves of *Indigofera arrecta* plant. In a preferred form of the invention, the powdered leaves are subjected to a hot water extraction process whereby the powdered leaves are contacted by hot water for a period of hours. The extract may be combined with an excipient carrier material to prepare an admixture which may be encapsulated for oral administration. The admixture, which may preferably contain from about 2.6 to about 4.3% of the extract by weight, is preferably administered orally to a human patient afflicted by a peptic ulcer condition.

To prepare the extract, the leaves of *Indigofera arrecta*-plant are dried and reduced to a fine powder by grinding with a mortar and pestle or ball mill. 500 grams of the finely ground material are then macerated in 3 liters of water and heated over a boiling water bath for about 4 hours. The resultant mixture is then filtered using filter paper and the filtrate is concentrated in vacuo to a volume of about 800 ml. The concentrate is then freeze-dried for about 48 hours using a Finn Aqua Lyovac freeze dryer to provide a dry powder containing the active drug materials extracted from the initial powdered leaf material. The typical yield of the extracted material is about 14 to 15% based on the original weight of the crude ground leaf material. That is to say, the yield is about 70 to 75 grams when the starting batch is about 500 grams.

Phytochemical screening of the crude ground leaf material revealed the presence of volatile oils, saponins, tannins and resins. However, only tannins and saponins were found to be present in the freeze dried extract. Glycosides, anthraquinones, alkaloids, hydrolyzable tannins and resins were all absent from the freeze dried extract. The freeze dried extract contains about 0.02 to 0.04% by weight of volatile oils and about 7 to 9% by weight of tannins.

The *Indigofera arrecta* plant was selected as a possible candidate for scientific investigation in the first place and its effectiveness against bacteria known to be associated with peptic ulcer conditions was evaluated using the freeze dried extract. The minimum inhibitory concentration and minimum bactericidal concentration of *Indigofera arrecta* extract against *Ps. Aeruginosa, E. Coli, S. Aureus* and *B. Subtilis* were determined using the agar dilution method. *Indigofera arrecta* extract showed potent antimicrobial efficacy against all of the tested commonly encountered microbes. The minimum inhibitory concentrations were *Ps. Aeruginosa*, 0.5 mg/ml; *E. Coli*, 1 mg/ml; *S. Aureus*, 1 mg/ml; and *B. Subtilis*, 1 mg/ml. The minimum bactericidal concentrations were 1 mg/ml for *Ps. Aeruginosa* and 2 mg/ml for the other three bacteria species. Considering the spectrum of activity of *Indigofera arrecta* extract against all the test organisms, it could possibly be useful in treating other systemic bacterial infections.

The freeze dried extract of *Indigofera arrecta* leaves was subjected to acute toxicity test by the intraperitoneal route in mice using standard procedures. No remarkable adverse effect was observed. The $LD_{50}$ was established as 245±28 mg/kg i.p.

The target system in peptic ulcer disease is the gastrointestinal tract. Many anti-ulcer agents, especially those that interact with receptor systems, influence gastrointestinal physiology and its response to ulcerogenic substances. Based on this premise, the effect of the freeze dried hot water extract of *Indigofera arrecta* leaves and its interaction with acetylcholine (Ach) and histamine were investigated on both smooth muscles and skeletal muscles. The results indicate that the extract of *Indigofera arrecta* leaves may contain some anti-spasmodic principles which relax the smooth muscles of the gastrointestinal tract.

In a preliminary study, aspirin model of inducing experimental gastric ulcer in rats was used to assess the anti-ulcer activity of the extract of *Indigofera arrecta* leaves which is the subject of the invention. As shown in Table I, the extract of *Indigofera arrecta* leaves has a remarkable effect against aspirin-induced ulcers. This effect increased with the dose of the extract as shown by the mean ulcer indices.

TABLE I

| Dose of *I. arrecta* extract | Ulcer Index |
| --- | --- |
| Normal saline solution | 1.1 ± 0.07 |
| 250 mg of extract/ml of saline | 0.5 ± 0.12 |
| 500 mg of extract/ml of saline | 0.24 ± 0.02 |

Drugs that delay the small intestinal transit time have beneficial effects on ulcer patients. The effect of the *Indigofera arrecta* extract on small intestinal transit in mice was tested using the charcoal meal method. The results in Table II below show that intraperitoneal administration of the extract in mice significantly reduced small intestinal transit. The inhibition, however, did not seem to be dose-dependent.

TABLE II

| Dose of extract | % distance traveled | % inhibition |
|---|---|---|
| Normal saline soln. | 92.38 ± 8.8 | 7.4 |
| 250 mg/ml of saline | 33.93 ± 1.2 | 66.07 |
| 500 mg/ml of saline | 61.16 ± 11.3 | 38.8 |
| Noradrenaline | 64.6 ± 9.0 | 35.4 |

The *Indigofera arrecta* extract of the invention showed little tendency to induce inflammation. In fact, during testing the extract was administered i.p. (200 mg/kg) for 1 hour before inflammation was induced. On the other hand, the *Indigofera arrecta* extract at the dose tested did not exhibit potent anti-inflammatory activity. Significant ($P<0.05$) anti-inflammatory activity was observed, however, 80 min. after egg-albumin.

The analgesic effect of the *Indigofera arrecta* extract of the invention was tested in thermal pain (Hot plate at 50.2±1° C.) and chemical pain (acetic acid induced writhing). in the two models, it appeared that the *Indigofera arrecta* extract was ineffective in increasing pain threshold.

Antisecretory activity of the *Indigofera arrecta* extract of the invention was also studied. This study was performed in pylorus—ligated (sham) rats. After 48 hours fasting with access to water ad libitum, the pylorus was ligated under pentobarbitone anaesthesia. Pylorus ligation of the rats for 6 hours caused accumulation of gastric secretory volume and increased gastric acid output. As shown below in Table III, the *Indigofera arrecta* extract of the invention significantly decreased the volume and acidity of basal gastric secretions. The number and severity of ulcer were remarkably reduced in animals treated with the *Indigofera arrecta* extract of the invention. Moreover, it was determined that the effect of the extract was dose dependent.

TABLE III

| Treatment Dosage/Kg | Volume of gastric secretion | Acid Output (mEq/L) |
|---|---|---|
| 40 ml saline | 3.6 ± 0.19 | 250 ± 16.4 |
| 50 mg *I. arrecta* extract | 2.6 ± 0.99 | 170 ± 6.8 |
| 100 mg *I. arrecta* extract | 2.3 ± 0.12 | 150 ± 8.2 |

The *Indigofera arrecta* plant leave extract of the invention was standardized and formulated into capsule dosage forms using World Health Organization (WHO) guidelines. These guidelines clearly advise that when a plant based product (e.g. herbal medicine) is safe and indicates efficacy, it can be subsequently standardized and formulated into suitable dosage for clinical trials. In accordance with accepted procedures it has been determined that an appropriate daily dosage of the *Indigofera arrecta* plant leave extract of the present invention is approximately 2.5 to 5 mg/Kg of body weight administered orally in two divided doses.

Clinical trials for the *Indigofera arrecta* leave extract of the invention commenced using volunteers. The clinical parameter of episodic pain, nausea and vomiting as well as kidney and liver hematological status and function were assessed. The data obtained so far indicates the efficacy of the *Indigofera arrecta* plant leave extract against peptic ulcer with no detectable adverse effects on kidney, liver and blood chemistry. The values recorded for these parameters fall within normal ranges. On the average about 80% of those in the test groups have experienced relief from episodes of pain since they entered the test program.

As a result of the testing to date, it has been determined that an appropriate and effective formulation of the *Indigofera arrecta* plant leave extract of the invention for oral administration to humans for managing peptic ulcer conditions includes about 8 to 12 parts by weight of the extract itself, about 170 to 130 parts by weight of heavy magnesium carbonate, about 100 to 120 parts by weight of dried maize starch and about 4 to 6 parts by weight of a mixture of talc and magnesium stearate. This formulation is prepared by adsorbing about 200 mg of the freeze dried extract, which has a sticky solid mass, in about 20 to 25 ml of methanol. The mixture is subjected to evaporation over a water bath leaving a thick liquid mass. About 3 to 4 grams of heavy magnesium carbonate is added as an agent for adsorption, after which the mixture is triturated to present a homogenous mass. About 2 to 2.4 grams of dried maize starch is then added and the mixture again triturated to form a uniform mixture. About 3 to 12 mg of a talc/magnesium stearate mixture is then added and again the mass is mixed until uniformity is attained. The material is then filled into capsules such that each capsule contains from about 232 to 306 mq of the uniform mixture. The daily dose of the *Indigofera arrecta* plant leave extract of the invention then is administered orally as two separate capsules, preferably one in the morning at breakfast time and the other in the evening before bed.

We claim:

1. An orally administratable human dose form of a therapeutic peptic ulcer palliating composition comprising an amount of a water extract of *Indigofera arrecta* plant leaves effective for peptic ulcer palliation in a human being and an excipient carrier for said extract.

2. A dose form as set forth in claim 1, wherein said comprises a hot water extract of *Indigofera arrecta* plant leaves.

3. A dose form as set forth in claim 1, wherein said excipient carrier comprises magnesium carbonate, dried maize starch, talc and magnesium stearate.

4. A dose form as set forth in claim 3, wherein said composition comprises from about 8 to about 12 parts by weight of said leaf extract, from about 170 to about 180 parts by weight of said magnesium carbonate, from about 100 to about 120 parts by weight of said dried maize starch and from about 4 to about 6 parts by weight of a talc/magnesium stearate mixture.

5. A dose form as set forth in claim 1, wherein said composition comprises from about 2.6 to about 4.3% by weight of said extract.

6. A dose form as set forth in claim 4, wherein said composition comprises from about 2.6 to about 4.3% by weight of said extract.

* * * * *